US006368622B2

United States Patent
Chen et al.

(10) Patent No.: US 6,368,622 B2
(45) Date of Patent: *Apr. 9, 2002

(54) PROCESS FOR PREPARING SOLID FORMULATIONS OF LIPID REGULATING AGENTS WITH ENHANCED DISSOLUTION AND ABSORPTION

(75) Inventors: Yisheng Chen, Gurnee; Kevin R. Engh, Mundelein; Yihong Qiu, Gurnee; Thomas L. Reiland, Gages Lake, all of IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/240,515

(22) Filed: Jan. 29, 1999

(51) Int. Cl.⁷ .............................. A61K 9/20; A61K 9/48
(52) U.S. Cl. ....................... 424/464; 424/465; 424/452; 424/451
(58) Field of Search ................................ 424/451, 452, 424/464, 465

(56) References Cited

U.S. PATENT DOCUMENTS

| 4,058,552 A | 11/1977 | Mieville ...................... 560/52 |
| 4,739,101 A | 4/1988 | Bourgogne et al. ........... 560/61 |
| 4,800,079 A | 1/1989 | Boyer ......................... 424/482 |
| 4,895,726 A | 1/1990 | Curtet et al. ................. 424/456 |
| 4,957,746 A | 9/1990 | Valducci |
| 4,961,890 A | 10/1990 | Boyer ......................... 264/113 |
| 5,082,655 A * | 1/1992 | Snipes et al. ............... 424/386 |
| 5,545,628 A | 8/1996 | Deboeck et al. |
| 5,645,856 A | 7/1997 | Lacy et al. .................. 424/455 |
| 5,880,148 A | 3/1999 | Edgar et al. |

FOREIGN PATENT DOCUMENTS

| EP | 0793958 | 2/1997 |
| WO | 8201649 | 5/1982 |

OTHER PUBLICATIONS

Ming–Thau Sheu et al., Characterization and Dissolution of Fenofibrate Solid Dispersion Systems, *International Journal of Pharmaceutics*, (1994), p. 137–146.

G. F. Palmieri et al., Characterization and Dissolution Studies of PEG 4000/Fenofibrate Solid Dispersions, *S.T.P. Pharma Sciences*, (1996), pp. 188–194.

* cited by examiner

*Primary Examiner*—James M. Spear
(74) *Attorney, Agent, or Firm*—Rockey, Milnamow & Katz, Ltd

(57) ABSTRACT

A process for preparing a solid formulation of a lipid-regulating agent comprising forming a mixture of said lipid-regulating agent with a surfactant; granulating said mixture by melting, mixing, and congealing said mixture; and optionally forming a finished dosage form.

15 Claims, 2 Drawing Sheets

PROCESS FOR PREPARING SOLID FORMULATIONS OF LIPID REGULATING AGENTS WITH ENHANCED DISSOLUTION AND ABSORPTION

FIELD OF THE INVENTION

The present invention relates to a new process for preparing solid formulations of lipid-regulating agents with enhanced dissolution and absorption characteristics.

BACKGROUND OF THE INVENTION

2-[4-(4-chlorobenzoyl)phenoxy]-2-methyl-propanoic acid, 1-methylethylester, also known as fenofibrate, is representative of a broad class of compounds having pharmaceutical utility as lipid-regulating agents. More specifically, this compound is part of a lipid-regulating agent class of compounds commonly known as fibrates, and is disclosed in U.S. Pat. No. 4,058,552.

Fenofibrate has been prepared in several different formulations, c.f., U.S. Pat. No. 4,800,079 and U.S. Pat. No. 4,895,726. U.S. Pat. No. 4,895,726 discloses a co-micronized formulation of fenofibrate and a solid surfactant.

U.S. Pat. No. 4,961,890 discloses a process for preparing a controlled release formulation containing fenofibrate in an intermediate layer in the form of crystalline microparticles included within pores of an inert matrix. The formulation is prepared by a process involving the sequential steps of dampening said inert core with a solution based on said binder, then projecting said fenofibrate microparticles in a single layer onto said dampened core, and thereafter drying, before said solution based on said binder dissolves said fenofibrate microparticles, and repeating said three steps in sequence until said intermediate layer is formed.

European Patent Application No. EP0793958A2 discloses a process for producing a fenofibrate solid dosage form utilizing fenofibrate, a surface active agent and polyvinyl pyrrolidone in which the fenofibrate particles are mixed with a polyvinyl pyrrolidone solution. The thus obtained mixture is granulated with an aqueous solution of one or more surface active agents, and the granules thus produced are dried.

PCT Publication No. WO82/01649 discloses a fenofibrate formulation having granules that are comprised of a neutral core that is a mixture of saccharose and starch. The neutral core is covered with a first layer of fenofibrate, admixed with an excipient and with a second microporous outer layer of an edible polymer.

U.S. Pat. No. 5,645,856 discloses the use of a carrier for hydrophobic drugs, including fenofibrate, and pharmaceutical compositions based thereon. The carrier comprises a digestible oil and a pharmaceutically-acceptable surfactant component for dispersing the oil in vivo upon administration of the carrier, which comprises a hydrophilic surfactant, said surfactant component being such as not to substantially inhibit the in vivo lipolysis of the digestible oil.

The prior art processes obtained small particles of fenofibrate by the use of co-micronization of the drug with a surfactant. These resulting formulations may not have the maximized dissolution rate.

It is an object of the present invention to provide small particles of lipid-regulating agents, more preferably fenofibrate, having enhanced dissolution and absorption characteristics than those particles of such agents prepared by the prior art techniques.

SUMMARY OF THE INVENTION

The present invention is directed to a process for preparing a solid formulation of a lipid-regulating agent with enhanced dissolution and absorption characteristics.

This process comprises forming a mixture of the lipid-regulating agent with a solid surfactant, and granulating the mixture by melting, mixing, and congealing, then optionally forming a finished dosage form.

The mixture may be granulated by techniques well-known in the art, preferably by using a high shear granulator, a spinning disk or by spray congealing techniques.

The granules may be milled, if necessary, and optionally blended with conventional pharmaceutical excipients.

The finished oral dosage form may be prepared by techniques well-known to those skilled in the art by sizing the mixture, dry blending the resultant particles with excipients and forming the finished oral dosage form, preferably as a tablet or capsule.

The formulation thus produced may be administered directly as a granulated product, diluted into an appropriate vehicle for administration, encapsulated into soft or hard gelatin shells or capsules for administration, or administered by other means obvious to those skilled in the art.

DETAILED DESCRIPTION OF THE INVENTION

The bulk lipid-regulating agent can be prepared by any available method, as for example the compound fenofibrate may be prepared by the procedure disclosed in U.S. Pat. No. 4,658,552, or the procedure disclosed in U.S. Pat. No. 4,739,101, both herein incorporated by reference.

The lipid-regulating agent is mixed with a surfactant such as, for example, poloxamer polyols (Pluronic F68, B.F. Goodrich Specialty Chemicals). Other suitable surfactants include pharmaceutically-acceptable surfactants such as d-alpha tocopheryl polyethylene glycol succinate and polyoxyl 40 stearate.

The lipid-regulating agent/surfactant mixture is granulated by melting, mixing and congealing the mixture. Other excipients, such as starch, lactose, polyvinyl pyrrolidone and magnesium stearate may be added to the mixture. The mixture is then granulated, prefereably by use of a high shear granulator, a spinning disk or by spray drying techniques. The resulting material may be milled if necessary, and if desired, formed into a tablet or capsule by conventional techniques such as direct compression or other means.

The invention will be understood more clearly from the following non-limiting representative examples:

EXAMPLE 1

A. 4 grams of fenofibrate and 4 grams of Pluronic F68 (B.F. Goodrich Specialty Chemicals) were melted at 100° C. 2 grams of mannitol was added with mixing.

B. A second sample of 6 grams of fenofibrate was melted at 100° C. 12 grams of Pluronic F68 was added with mixing.

Each mixture was congealed at room temperature with stirring. The congealed solids were milled through a 30 mesh screen using a Quadro Comill. The resultant powder/granules were collected and #2 capsules were filled with 167.5 mg of granules from Example 1A (67 mg fenofibrate) and 134 mg of granules from Example 1B (67 mg of fenofibrate).

EXAMPLE 2

Fenofibrate and Pluronic F68 were melted and mixed in a 1:2 weight ration in a container at approximately 100° C. followed by congealing while mixing at room temperature. The particle size of the congealed solid was reduced to below 30 mesh by grinding and sieving. Granules containing 67 mg of fenofibrate were filled into #2 hard gelatin capsules.

The in vitro dissolution rate of the capsules of Example 1B was compared with that of capsules of Lipanthyl®, a commercial capsule product containing 67 mg of fenofibrate. USP apparatus II was used for testing. The test conditions were: paddle speed=50 rpm; dissolution medium=50 mM SDS solution; temperature=37° C. Dissolution samples were analyzed by an HPLC method.

Figure 1:
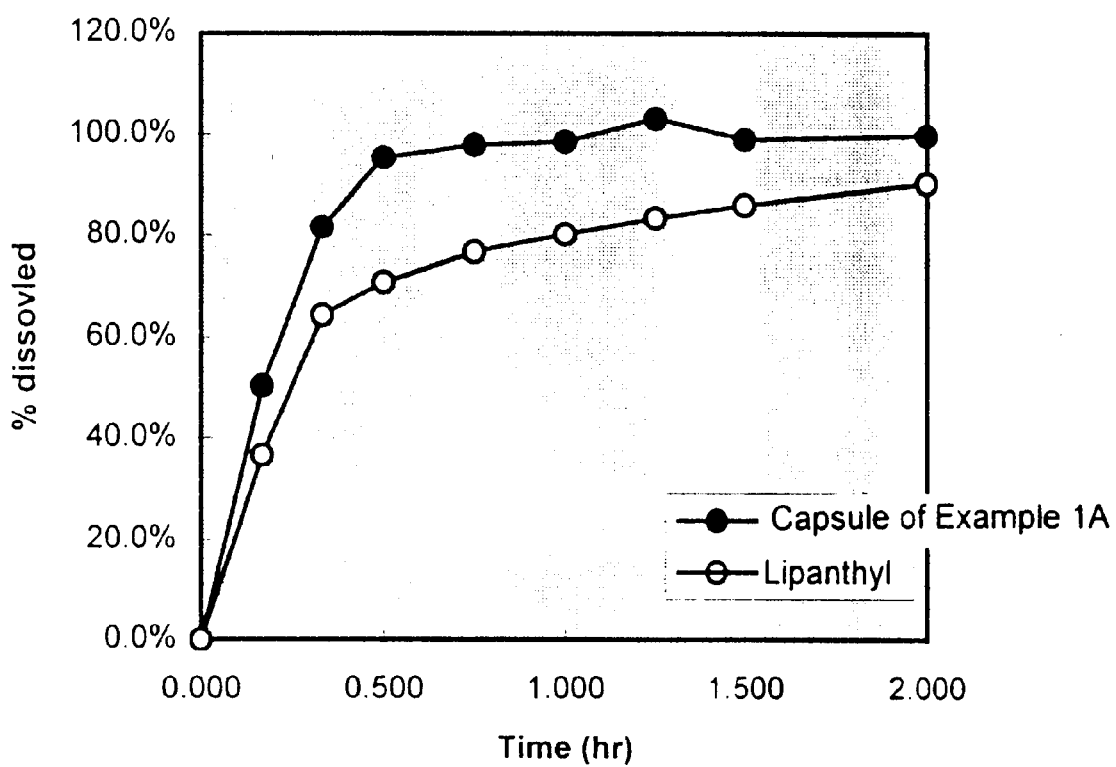
FIG. 1 is a graph showing the dissolution characteristics of a representative composition prepared by the process of the present invention and a prior art composition.
Figure 2:
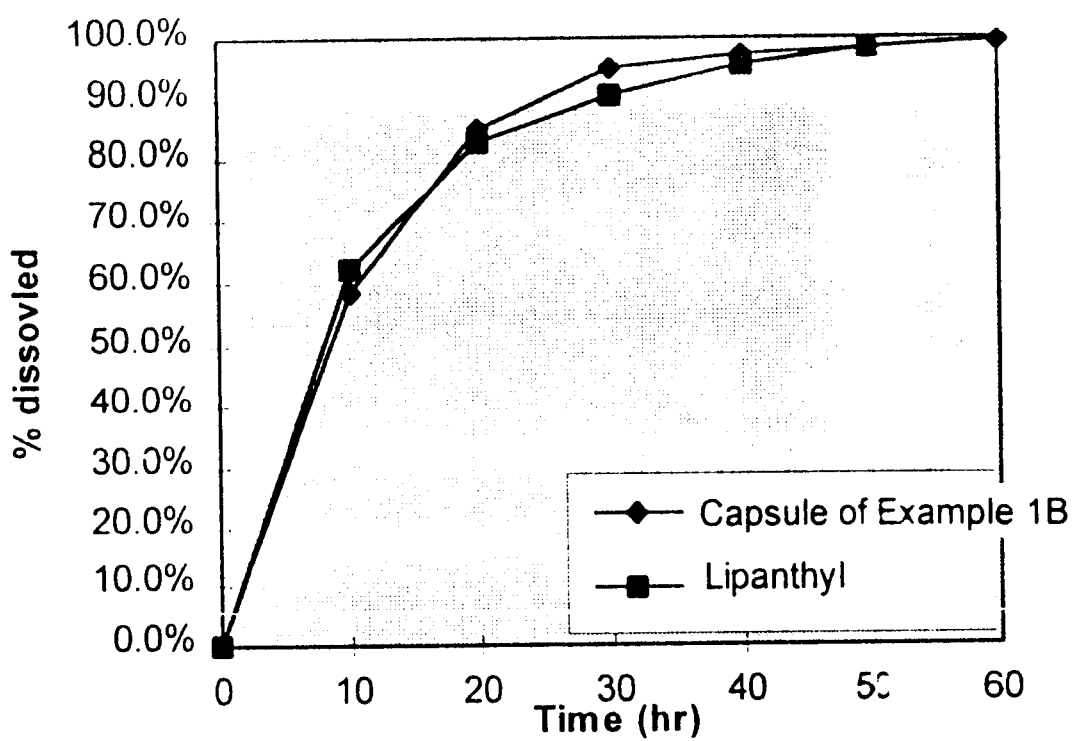
FIG. 2 is a graph showing the dissolution characteristics of another representative composition prepared by the process of the present invention and a prior art composition.

In vitro dissolution profiles of the reference capsule and capsules from Example 1 of the current invention are shown in FIGS. 1 and 2. This data indicates that dissolution rate of the current invention is more rapid and complete than the reference. Based on U.S. Pat. No. 4,895,726, in vitro dissolution results can be correlated to the in vivo bioavailability in humans. Thus, more rapid and complete dissolution in vitro can result in higher bioavailability in humans.

EXAMPLE 3

Fenofibrate, Pluronic F68 and mannitol (4:4:2 weight ratio) were melted and mixed in a container at approximately 100° C. followed by congealing while mixing at room temperature. Particles of the congealed solid were milled through a 30 mesh screen using Quadro Comill. Granules equivalent to 67 mg fenofibrate were filled into a #2 hard gelatin capsule.

In vitro dissolution rate of the capsules of Example 1A were compared with that of the reference, Lipanthyl, the marketed capsule product, which contains the same amount of the active ingredient. USP apparatus II was used for testing. The test conditions were: paddle speed=75 rpm; dissolution medium=100 mM SDS solution; temperature=37° C. Dissolution samples were analyzed by an HPLC method.

In vitro dissolution profiles of the reference capsule and capsules from Example 1A of the present invention are shown in FIG. 2. Preliminary data indicate that dissolution rate of such capsule of the current invention is equivalent to the reference. Based on U.S. Pat. No. 4,895,726, in vitro dissolution result can be correlated to the in vivo bioavailability in humans. Thus, equivalent dissolution in vitro can result in equivalent bioavailability in humans.

What is claimed is:

1. A process for preparing a solid formulation of a fibrate having more rapid dissolution comprising the steps of:

forming a mixture of said fibrate with a surfactant;

granulating said mixture by melting, mixing, and congealing said fibrate and said surfactant,
optionally with one or more excipients;

and optionally forming a finished dosage form.

2. A process for preparing a solid formulation of a fibrate comprising the steps of:

forming a mixture of said fibrate with a surfactant;

granulating said mixture by melting, mixing, and congealing,
optionally with one or more excipients;

and optionally forming a finished dosage form.

3. A process of claim 2 wherein the fibrate is fenofibrate.

4. A process of claim 1 wherein said surfactant is selected from the group consisting of sodium lauryl sulfate, poloxamer polyols, block copolymers of ethylene oxide and propylene oxide, d-alpha tocopheryl polyethylene glycol succinate and polyoxyl 40 stearate.

5. The process of claim 4 wherein said surfactant is polyoxamer polyols.

6. A process of claim 1 further comprising adding one or more excipients to the granulated mixture.

7. A process of claim 6 wherein the excipient is a pharmaceutically-acceptable excipient selected from the group consisting of lactose, starch, polyvinyl pyrrolidone and magnesium stearate.

8. A process of claim 1 wherein the granulated mixture is milled.

9. A process of claim 1 further comprising preparing a finished dosage form.

10. A process for preparing a solid formulation of a fibrate having more rapid dissolution comprising the steps of:

forming a mixture of said fibrate with a surfactant;

granulating said mixture by melting, mixing, and congealing, said fibrate and said surfactant,
optionally with one or more excipients;

and forming a tablet.

11. A process of claim 9 where the finished dosage form is a capsule.

12. A composition prepared by the process of claim 1.

13. A composition prepared by the process of claim 3.

14. A method for treating of hyperlipidemia comprising the administration of a formulation prepared by the process of claim 1.

15. A method for treating of hyperlipidemia comprising the administration of a formulation prepared by the process of claim 3.

* * * * *